United States Patent
Baird et al.

(10) Patent No.: US 10,912,526 B1
(45) Date of Patent: Feb. 9, 2021

(54) RADIATION SCATTER ANESTHESIA PROTECTION SYSTEM

(71) Applicants: David A. Baird, Rome, OH (US); Thomas P. Hink, Euclid, OH (US); Denio A. Leone, Rocky River, OH (US)

(72) Inventors: David A. Baird, Rome, OH (US); Thomas P. Hink, Euclid, OH (US); Denio A. Leone, Rocky River, OH (US)

( * ) Notice: Subject to any disclaimer, the term of this patent is extended or adjusted under 35 U.S.C. 154(b) by 0 days.

(21) Appl. No.: 16/578,515

(22) Filed: Sep. 23, 2019

(51) Int. Cl.
  *A61B 6/10* (2006.01)
  *G21F 3/00* (2006.01)
  *A61B 6/04* (2006.01)

(52) U.S. Cl.
  CPC .............. *A61B 6/107* (2013.01); *G21F 3/00* (2013.01); *A61B 6/0407* (2013.01)

(58) Field of Classification Search
  CPC ..... A61B 6/107; A61B 6/0407; A61B 6/4423; G21F 3/00; G21F 1/125; G21F 1/106; G21F 3/03; G21F 1/12
  USPC ......... 250/519.1, 515.1, 516.1, 505.1, 517.1, 250/518.1; 128/849; 211/85.8
  See application file for complete search history.

(56) References Cited

U.S. PATENT DOCUMENTS

| | | | | |
|---|---|---|---|---|
| 5,417,225 A | * | 5/1995 | Rubenstein | A61B 90/04 128/849 |
| 7,829,873 B2 | * | 11/2010 | Fox | A61B 6/107 250/515.1 |
| 2013/0270462 A1 | * | 10/2013 | Beck | A47B 83/00 250/516.1 |
| 2014/0048730 A1 | * | 2/2014 | Niedzielski | A61B 6/107 250/519.1 |
| 2017/0258417 A1 | * | 9/2017 | Hoornaert | A61B 6/547 |
| 2019/0189300 A1 | * | 6/2019 | Rauth | G21F 1/125 |
| 2019/0350542 A1 | * | 11/2019 | Baird | G21F 1/125 |

* cited by examiner

*Primary Examiner* — David A Vanore
(74) *Attorney, Agent, or Firm* — Daniel M. Cohn; Howard M. Cohn (57) ABSTRACT

A radiation scatter anesthesia protection system designed to attach to a procedure table to limit exposure to radiation for both medical staff and a patient. The radiation scatter anesthesia protection system includes a headboard adapted to be disposed adjacent the patient's head. Headboard shielding including a first sheet of shielding extending downward from the procedure table, a plurality of additional sheets of shielding removably mounted to the headboard, and a molded head shield extending from the headboard. A frame disposed adjacent the procedure table. First and second outer side curtain shields suspended from the frame. First and second central curtain shields disposed between the first and second outer side curtain shields and suspended from the frame.

20 Claims, 6 Drawing Sheets

RADIATION SCATTER ANESTHESIA PROTECTION SYSTEM

CROSS REFERENCE TO RELATED APPLICATIONS

This application relates to U.S. Utility patent application Ser. No. 16/414,375 filed on May 16, 2019.

TECHNICAL FIELD OF THE INVENTION

The present invention relates to a radiation scatter protection system, and more particularly to protection system designed to limit exposure to radiation for both medical staff and patients.

BACKGROUND OF THE INVENTION

In the medical field, personnel are often required to work in close proximity to patients undergoing imaging procedures involving x-rays, commonly referred to as fluoroscopy. The hazard to the worker arises from x-rays scattered by the patient's body toward the worker. Although such scattered radiation has a lower energy level than the direct x-ray beam, it does maintain its ionizing potential. Exposure to this scattered radiation has the potential to produce a significant radiation hazard over the working lifetime of the worker. For this reason, workers traditionally wear a radiation shielding garment that places a protective barrier between the scattering tissues of the patient and the body of the worker.

Traditionally such garments are made from a flexible rubber or polymer material within which is embedded powdered lead, a good absorber of x-rays. Unfortunately, lead garments are heavy and can cause significant injury to the wearer with daily use over a working lifetime. There has thus begun a search for lighter weight materials which can provide equivalent protection under the conditions of this job.

An underlying principle of such reduced weight garments is that for a large portion of the x-ray energy levels commonly used in medical procedures, certain elements, provide greater attenuation per unit weight than lead. Until now, most workers have assumed that the testing of the effectiveness of such elements, such as Antimony and Bismuth, other than lead requires meeting the requirements of shielding from the effects of the direct x-ray beam from the x-ray source.

It is now realized, however, that the danger to the worker is primarily caused by radiation reflected from the patient's body, so-called "scattered radiation". An additional problem, however, arises from the fact that many of these lower atomic number heavy metals reradiate the x-rays they absorb, albeit at lower energy levels. This can lead to a problem where the exposure to the wearer is greater than that evident from the attenuation tests.

SUMMARY OF THE INVENTION

According to an embodiment of the present invention, there is disclosed a radiation scatter anesthesia protection system designed to attach to a procedure table to limit exposure to radiation for both medical staff and a patient. The radiation scatter anesthesia protection system includes a headboard adapted to be disposed adjacent the patient's head. Headboard shielding including a first sheet of shielding extending downward from the procedure table, a plurality of additional sheets of shielding removably mounted to the headboard, and a molded head shield extending from the headboard. A frame disposed adjacent the procedure table. First and second outer side curtain shields suspended from the frame. First and second central curtain shields disposed between the first and second outer side curtain shields and suspended from the frame.

According to an embodiment of the present invention, there is disclosed a radiation scatter anesthesia protection system designed to attach to a procedure table to limit exposure to radiation for both medical staff and a patient. The radiation scatter anesthesia protection system includes a headboard of Polyethylene Terephthalate Glycol (PETG) adapted to be disposed adjacent the patient's head. Headboard shielding including a first sheet of shielding extending downward from the procedure table, a plurality of additional sheets of shielding removably mounted to the headboard, and a molded head shield extending from the headboard. A frame disposed adjacent the procedure table. First and second outer side curtain shields suspended from the frame. The first and second central curtain shields being disposed between the first and second outer side curtain shields and suspended from the frame. The headboard shielding, the first and second outer side curtain shields, and the first and second central curtain shields are constructed of sheets of lead-impregnated rubber.

BRIEF DESCRIPTION OF THE DRAWINGS

The structure, operation, and advantages of the present invention will become further apparent upon consideration of the following description taken in conjunction with the accompanying figures (Figs.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

In the drawings accompanying the description that follows, both reference numerals and legends (labels, text descriptions) may be used to identify elements. If legends are provided, they are intended merely as an aid to the reader, and should not in any way be interpreted as limiting.

DETAILED DESCRIPTION OF THE PREFERRED EMBODIMENTS

In the description that follows, numerous details are set forth in order to provide a thorough understanding of the present invention. It will be appreciated by those skilled in the art that variations of these specific details are possible while still achieving the results of the present invention. Well-known processing steps are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

In the drawings accompanying the description that follows, often both reference numerals and legends (labels, text descriptions) will be used to identify elements. If legends are provided, they are intended merely as an aid to the reader, and should not in any way be interpreted as limiting.

Physicians and allied clinical personnel, collectively referred to as medical staff, are commonly involved in medical procedures involving patients in which fluoroscopic and other types of radiation systems (such as computer tomography, or CT systems) are used for purposes of diagnostic detection or guidance procedures. These radiation systems allow the medical staff to peer into the body systems of a patient with minimal invasiveness. The images generated may be in the form of a single image, or a video feed, both of which may be live. For example, the anatomy of a patient may be illuminated using x-rays so that the medical staff can carry out medical procedures using a fluoroscopic viewing screen. In one case, x-ray fluoroscopy may be used to indirectly guide the placement of a surgical device within the patient during a surgical procedure.

When working with a patient on a procedure table, doctors and other medical personnel can be exposed to primary radiation that emanates directly from the source and/or exposed to secondary radiation that is scattered by an object such as the x-ray detector, the procedure table, and even the patient. Traditionally, there have been apparatuses and methods for protecting and shielding against radiation in x-ray laboratories. Though there are numerous shapes and designs for protective shields, and although they may be constructed of various materials, they do not sufficiently protect against radiation exposure, and thus medical personnel must still wear heavy and encumbering leaded protective clothing.

The radiation scatter anesthesia protection system 10 is designed to limit exposure to radiation for both medical staff and patients, but particularly for an anesthesiologist. It is also desirable to protect the anesthesiologist, the entire anesthesiologist team, and other medical staff members from radiation in a way that does not interfere or limit them from conducting their medical procedures.

FIGS. 1-6 illustrate the various components that collectively form the anesthesia protection system 10. In general terms, the anesthesia protection system 10 includes a plastic headboard 12, headboard shielding 14, first and second outer side curtain shields 16 and 18, first and second central curtain shields 20 and 21, and frame 22. The plastic headboard 12 and the various curtain shields described hereinafter are designed to minimize the risk of radiation exposure to both the anesthesiologist, who stands behind the anesthesia protection system 10, and the patient 24 laying on an x-ray bed 23 during a medical procedure requiring the use of X-rays and/or fluoroscopy. An aluminum rack to mount on the wall may be provided to store the elements of the anesthesia protection system 10.

Figure 2:
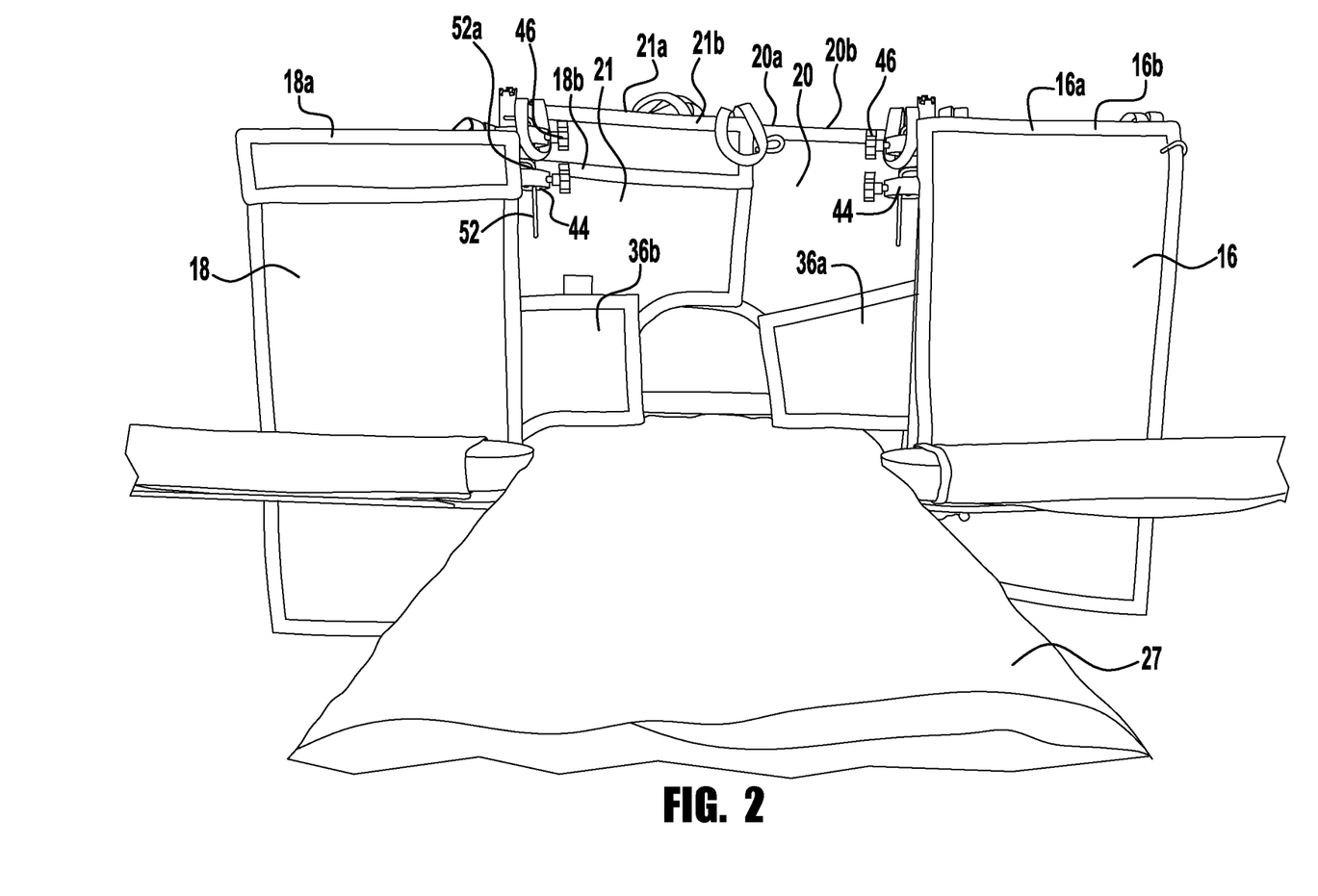
FIG. 2 is a rear, three-dimensional view of the anesthesia protection system and hospital bed, in accordance with the present invention.
Figure 3:
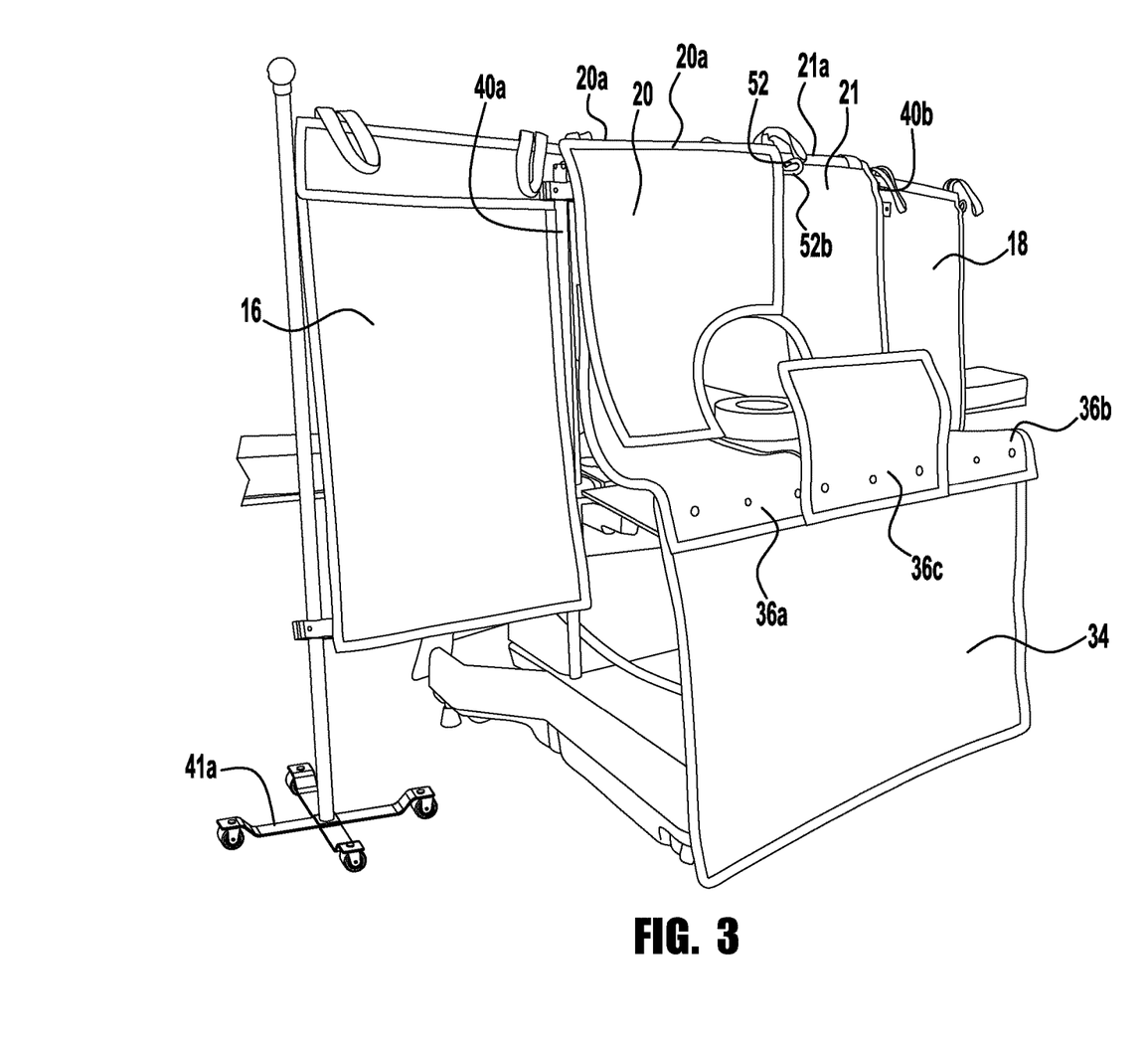
FIG. 3 is a front, three-dimensional view of the anesthesia protection system and hospital bed, in accordance with the present invention.
Figure 4:
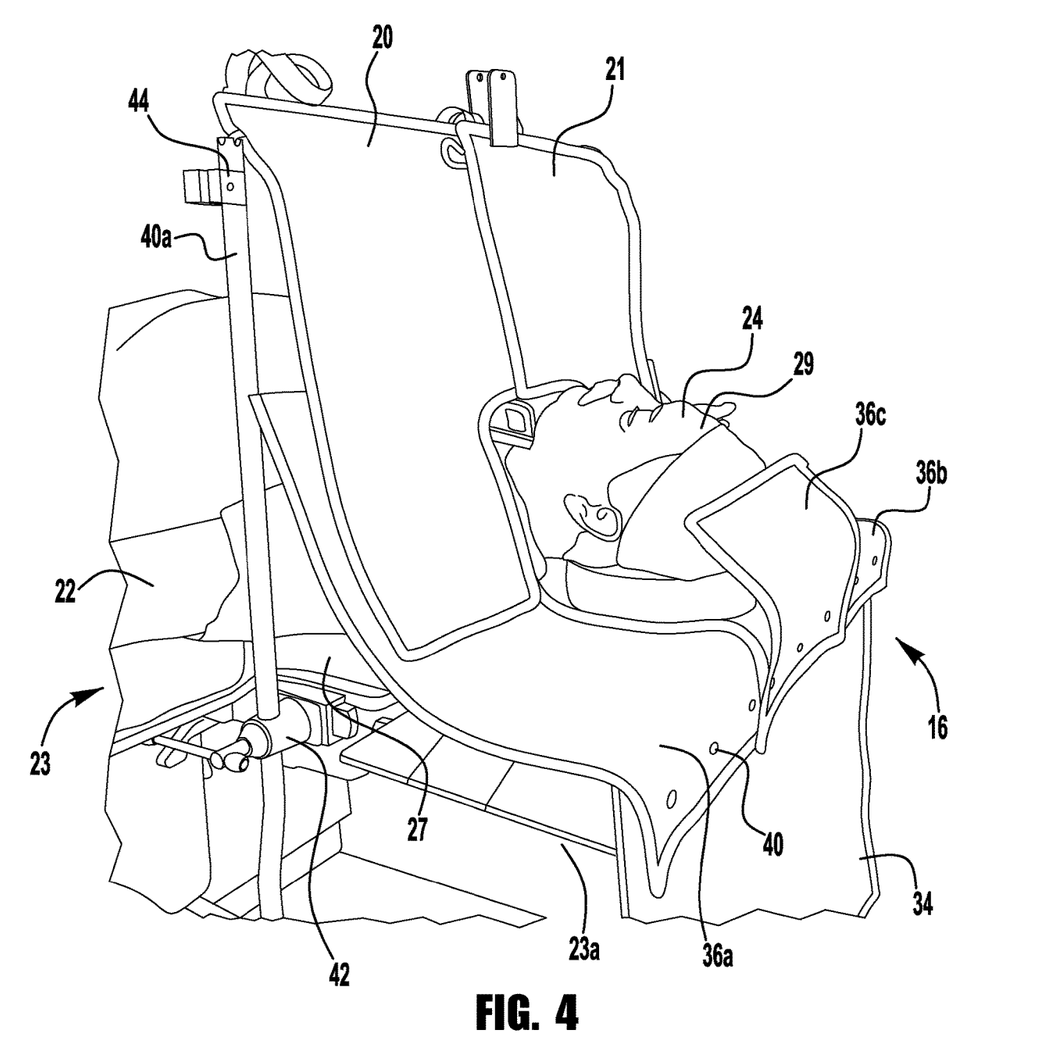
FIG. 4 is a side, three-dimensional view of the anesthesia protection system and in use with a patient on a hospital bed, in accordance with the present invention.

As illustrated in FIGS. 2, 3, and 4, the plastic headboard 12 is disposed on the front end 23a of a procedure table 23. The plastic headboard 12 is preferably manufactured from PETG (Polyethylene Terephthalate Glycol), also known as DACRON. DACRON is a condensation polymer obtained from ethylene glycol and terephthalic acid. Its properties include high tensile strength, high resistance to stretching, both wet and dry, and good resistance to degradation by chemical bleaches and to abrasion. The use of DACRON is advantageous for the present invention, since it is allows more X-rays to pass through headboard thickness than other plastics. The draw back to the use of PETG to form the plastic headboard is that the material is very hard to work with and to form the radius bend 26, described herein after, is extremely difficult and tedious.

Figure 6:
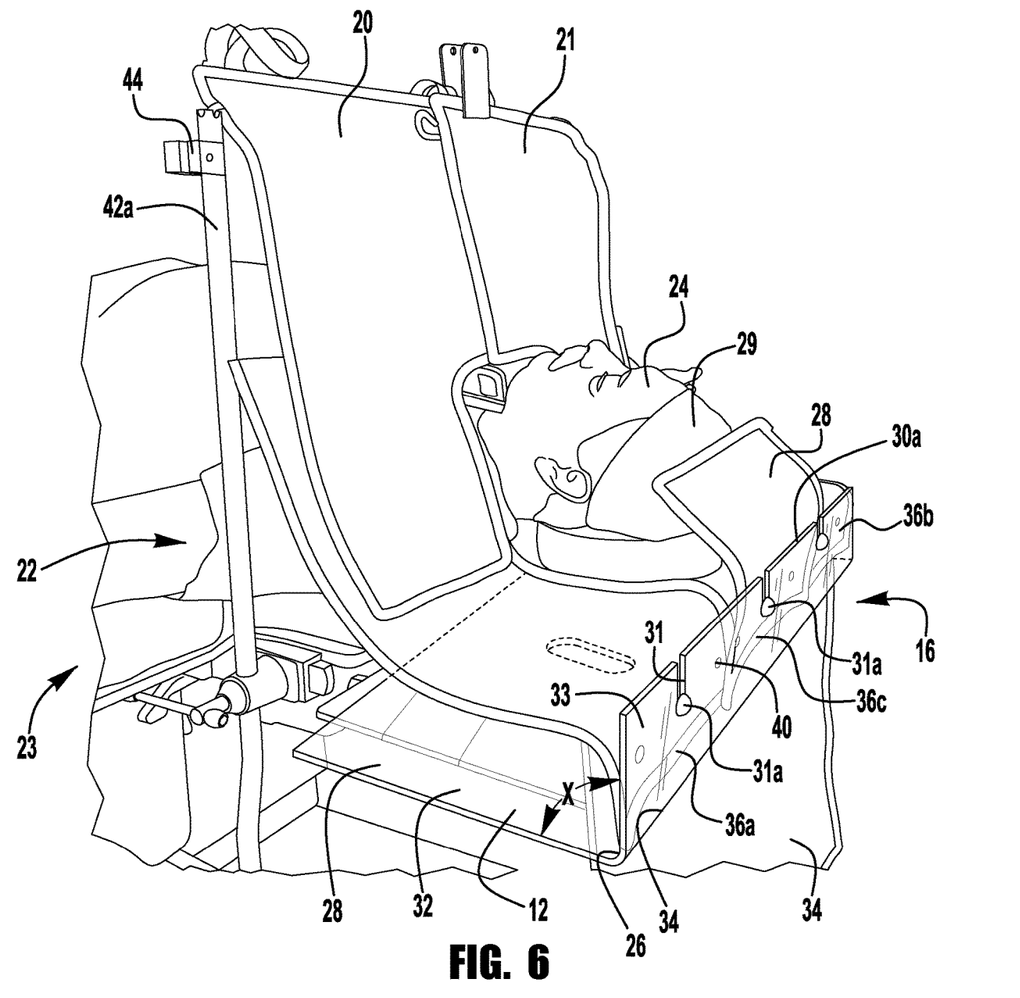
FIG. 6 is a side, three-dimensional view of the anesthesia protection system and hospital bed, in accordance with the present invention.

Preferably, the plastic headboard 12 is formed of an approximately ¼" thick PETG plastic sheet molded into an "L" shape with a first ¾" radius longitudinal bends 26, as seen in FIG. 6.

The plastic headboard 12 has exemplary overall dimensions of a horizontal leg 28 having a width W of about 11". A vertical leg 30 has a height H of about 2.5." The vertical leg 30 is preferably canted inward an angle x of about 5 and 15 degrees, and preferably about 10 degrees, off the perpendicular from the horizontal leg 28 to the vertical leg 30. The longitudinal bend 26 extends along the intersection of the horizontal leg 28 and the vertical leg 30.

The headboard 12 (as shown in FIG. 6) has a plurality of notches 31 cut into the vertical leg 30 and spaced along the length of the vertical leg 30 and extending from outer edge 30a of the leg 30. The notches 31 have exemplary dimensions of 1" in wide by 1" in length, although any desired dimensions may be utilized. In use, the notches 31 disposed through the headboard 12 accept corresponding knobs 31a protruding from the headboard shielding 14 to hold the headboard shielding in place.

As shown in FIGS. 4 and 6, with a patient 24 laying on a procedure table 23, the horizontal leg 28 of the headboard 12 is inserted under the procedure table mattress 27, and the vertical leg 33 extends upwardly from the procedure table and can rest against the patient's head. The patient's weight holds the headboard 12 in place.

The plastic headboard 12 blocks relatively less X-rays emitted from the emitter disposed under the procedure table 23 (not shown), so that the emitter in use can generate less X-rays then previously required. If the Image Intensifier (not shown) disposed above the patient senses that not enough X-ray light is coming through the patient, the Image Intensifier will cause the emitter to generate more X-rays. It's understood that the more X-rays the patient is subjected to, the more dangerous the procedure. Being that the plastic headboard 12 is constructed of DACRON, both the technician standing at the head of the table adjacent the patient's head and the patient themselves are at less risk of too much radiation exposure. This is because less X-rays are being generated specifically because the plastic headboard 12 is constructed of composite materials including DACRON that allows more X-rays to pass through the thickness of the headboard.

Figure 5:
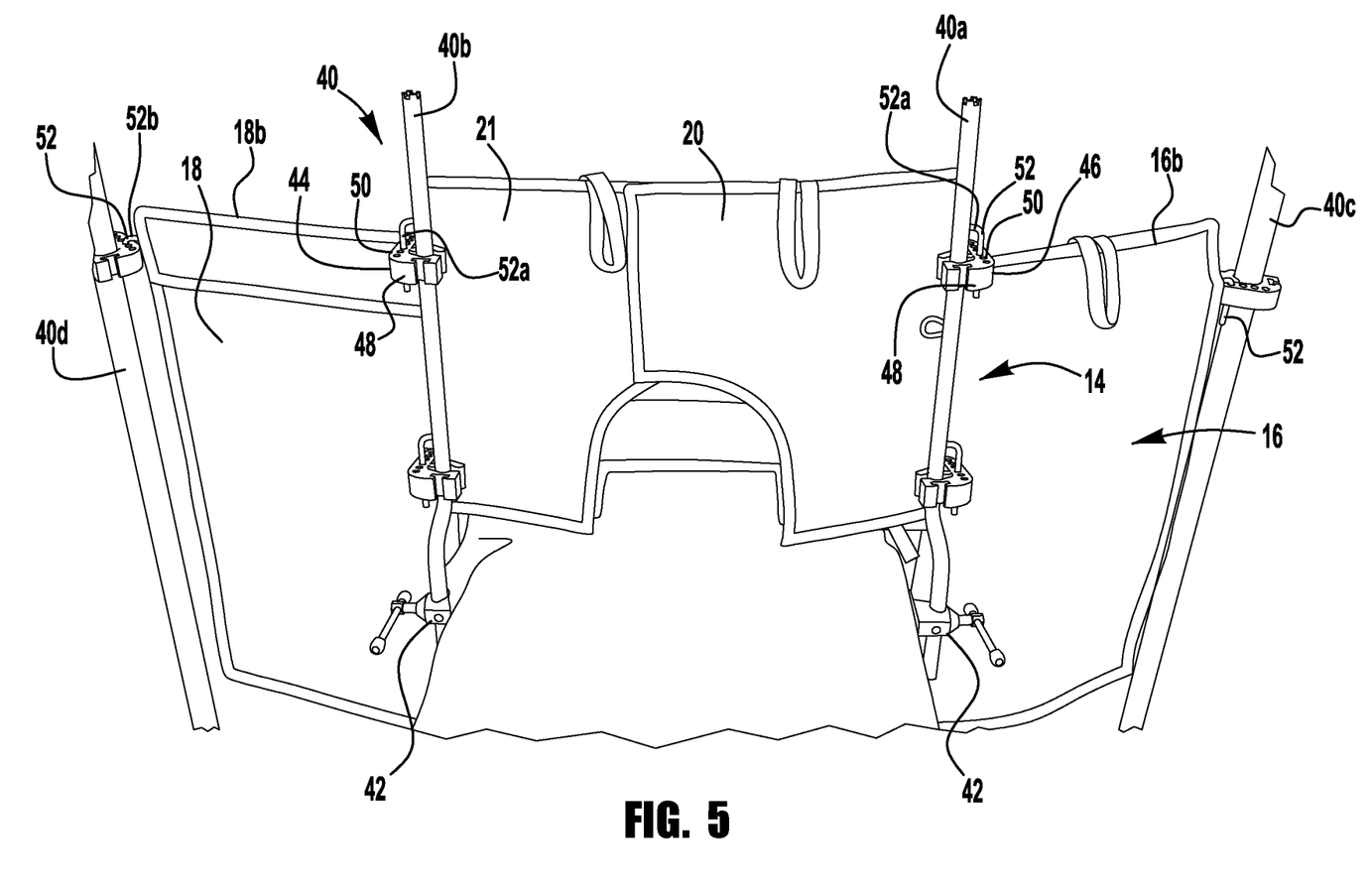
FIG. 5 is a rear, three-dimensional view of the anesthesia protection system and hospital bed, in accordance with the present invention.

FIGS. 5 and 6 illustrates the headboard shielding 14, which includes one larger sheet of shielding 34, extending downward from the top of table 23 to the floor. Two additional sheets of shielding 36a and 36b overlap the larger sheet of shielding 34 and are placed on the patient 24 and extend on the patient and above the table 23. The two sheets of shielding 36*a* and 36*b* have one end that drapes over the headboard 12. Additionally, a molded head shield 36 further extends from the headboard 12, to wrap about the head 29 of the patient 24, as seen in FIG. 4.

All the shielding described herein is preferably constructed of a sheet of lead-impregnated rubber covered on both the back and the front sides with 500 denier nylon cloth. The sheets of nylon cloth are sewn together around circumference of the shielding. The nylon cloth has a urethane coating on the inside surfaces that are disposed against the sheet of lead-impregnated rubber for water proofing.

The shielding 34, 36*a*, 36*b* and 36*c* are fastened together, such as with bolts 40 and all attach to a sheet of durable plastic sandwiched in between the bottom surface of the shields 36*a*, 36*b*, 36*c*, and the top surface of the sheet of shielding 34. The durable plastic sheet is typically approximately ¼" thick by 2" wide by 28" long and is provided to give lateral support to the shields. There are a plurality of knobs 31*a*, as seen in FIG. 6, bolted through the durable plastic sheet which correspond to the notches 31 of the plastic headboard 12.

The shielding 34 protects against radiation emitted from between the table 23 and the floor. The shielding 34 has exemplary dimensions of 30 inches wide by 22 inches high. The sheets of shielding 36*a* and 36*b* drape over the patient's shoulders and move independently from each other to allow medical personnel to move each piece of shielding independently when necessary to access a specific area of the patient's body.

In an exemplary embodiment, the sheet of shielding 36*a* will be 10 inches wide by 24 inches long, and the sheet of shielding 36*b* will be 10 inches wide by 24 inches long. The head shield 36*c* will be 12 inches wide by 10 inches long and have a generally concave shape to accommodate the patient's head 29. The shielding 34 will typically be positioned to hang down below the top part of the procedure table 23.

As illustrated in FIG. 5, there is a frame 40, consisting of a plurality of poles, typically constructed of metal. The frame 40 is designed to support the first and second outer side curtain shields 16 and 18, and the first and second central curtain shields 20 and 21.

It is within the terms of the embodiment that there be varying amount of poles to be used in relation with the anesthesia protection system 10.

Figure 1:
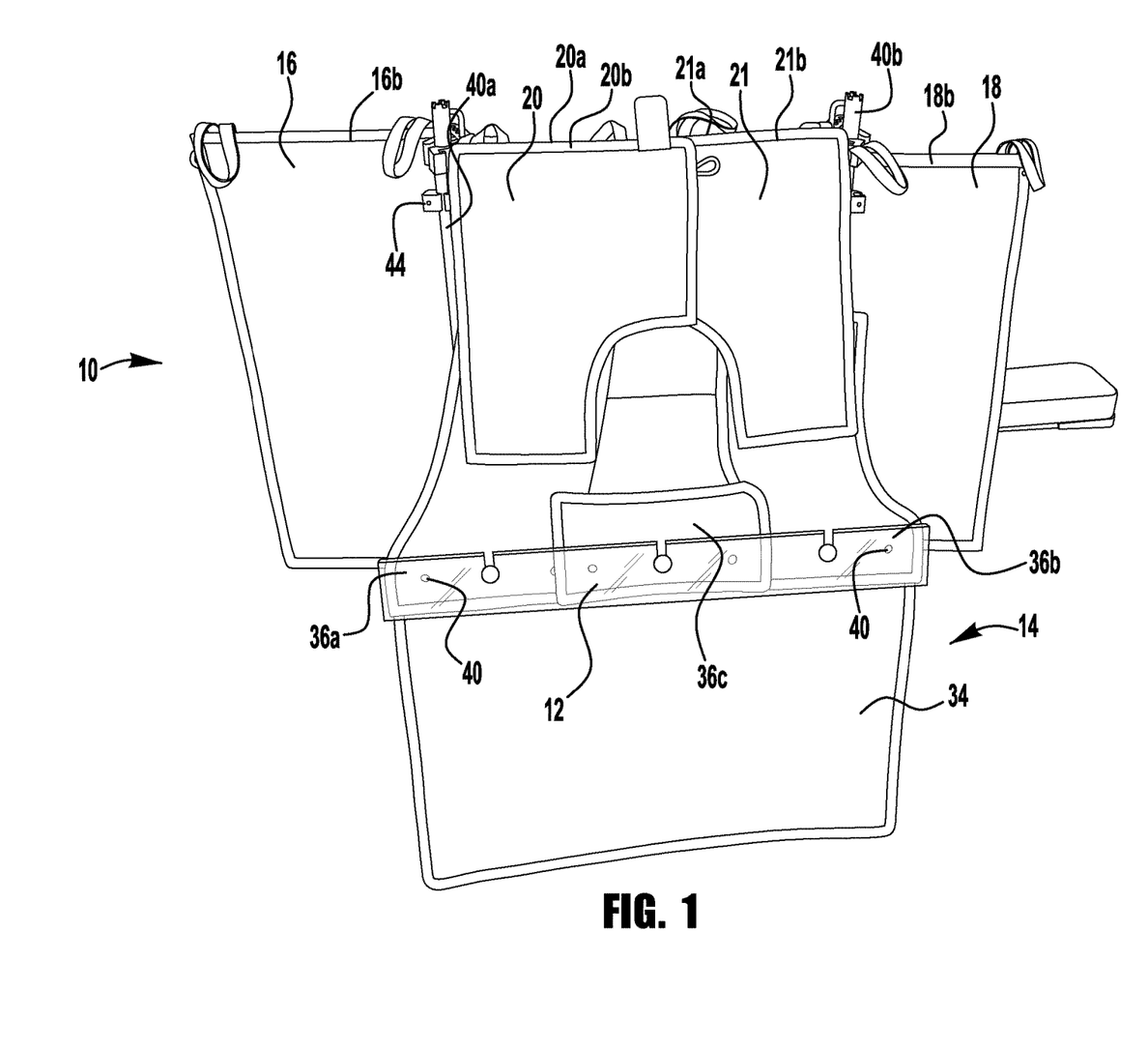
FIG. 1 is a front, three-dimensional view of the anesthesia protection system, in accordance with the present invention.

FIGS. 1 and 2 illustrate a first embodiment in which only first and second poles, 40*a* and 40*b* are utilized, supporting first and second outer side curtain shields 16 and 18, and the first and second central curtain shields 20 and 21. The poles 40*a* and 40*b* are preferably curved inwards, as illustrated in FIG. 5. Bed clamp 42 is attached to each of the first and second poles 40*a* and 40*b* to attach the poles to both sides of the table 23.

In the first embodiment, each of the first and second poles 40*a* and 40*b* incorporates two separate shield clamps 44. As described, one shield clamp 44 on first pole 40*a* supports the first side curtain shield 16, and a second shield clamp supports the first central curtain shield 20. Likewise, one shield clamp 44 on second pole 40*b* supports the second side curtain shield 18, and a second shield clamp supports the second central curtain shield 21. Shield clamps 44 typically are attached to an upper section of the first and second poles 40*a* and 40*b*. Each shield clamp 44 includes a threaded clamp tightener 46 to attach the shield clamp to the poles 40*a* and 40*b*, using a screw mechanism.

Each shield clamp 44 includes a bracket 48, having a plurality of holes 50 extending therethrough. Each of the plurality of holes 50 is designed to accommodate a pin 52. Each of the upper edges 16*a* and 18*a* of the first and second outer side curtain shields 16 and 18, respectively, includes a slit 16*b* and 18*b*, respectively, in the material to accommodate one of the pins 52. Thus, a first end 52*a* of the pin 52 is housed within a hole 50, and the second end 52*b* extends through the slits 16*b* and 18*b* to suspend the first and second outer side curtain shields 16 and 18.

Similarly, each of the upper edges 20*a* and 21*a* of the first and second central curtain shields 20 and 21, respectively, includes a slit 20*b* and 21*b*, respectively, in the material to accommodate one of the pins 52. Thus, a first end 52*a* of the pin 52 is housed within a hole 50, and the second end 52*b* extends through the slits 16*b* and 18*b* to suspend the first and second central curtain shields 20 and 21.

FIGS. 3 and 5 illustrates a second embodiment in which, the first and second poles, 40*a* and 40*b* support the first and second central curtain shields 20 and 21. Third and fourth poles 40*c* and 40*d* support first and second outer side curtain shields 16 and 18. The third and fourth poles 40*c* and 40*d* are typically free standing on a wheeled base 41*a* and 41*b*, respectively, for ease of movement.

In the second embodiment, each of the first and second poles 40*a* and 40*b* incorporate one shield clamps 44. As described, one shield clamp 44 on first pole 40*a* supports the first central curtain shield 20, and one shield clamp 44 on the second pole 40*b* supports the second central curtain shield 21. Further, one shield clamp 44 on third pole 40*c* supports the first side curtain shield 16, and one shield clamp 44 on the fourth pole 40*d* supports the second side curtain shield 18.

In terms of use and functionality, the second embodiment functions similarly to the first embodiment, with the exception that each of the poles 40*a*, 40*b*, 40*c*, and 40*d* has its own shield clamp 44.

The first and second outer side curtain shields 16 and 18 are in mirror orientation to each other, when suspended, as seen in FIG. 2. The first and second outer side curtain shields 16 and 18 are preferably constructed of a sheet of lead-impregnated rubber covered on both the back and the front sides with two sheets of 500 denier nylon cloth covering and sewn together around circumference of the shielding. The nylon cloth has a urethane coating on the inside surfaces against the sheet of lead-impregnated rubber for water proofing. In an exemplary embodiment, the first and second outer side curtain shields 16 and 18 will be 15 inches wide by 30 inches long.

The first and second central curtain shields 20 and 21 are in mirror orientation to each other, when suspended, as seen in FIG. 2. The first and second outer side curtain shields 16 and 18 are preferably constructed of a sheet of lead-impregnated rubber covered on both the back and the front sides with two sheets of 500 denier nylon cloth covering and sewn together around circumference of the shielding. The nylon cloth has a urethane coating on the inside surfaces against the sheet of lead-impregnated rubber for water proofing An aluminum rack (not shown) may be included and formed of a long solid aluminum bar. The rack includes one or more holes, and one or more pins looped over the top edge of the aluminum bar. Typical dimensions of the rack is ½" thick by 3" wide by 20" long. The rack is utilized to neatly hang the various lead shielding components, described herein, so that they are not draped over other equipment in the room or hungover devices which take up further space in the procedure room.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

The invention claimed is:

1. A radiation scatter anesthesia protection system designed to attach to a procedure table to limit exposure to radiation for both medical staff and a patient, comprising;
   a headboard adapted to be disposed adjacent the patient's head;
   headboard shielding including a first sheet of shielding extending downward from the procedure table, a plurality of additional sheets of shielding removably mounted to the headboard, and a molded head shield extending from the headboard;
   a frame disposed adjacent the procedure table;
   first and second outer side curtain shields suspended from the frame; and
   first and second central curtain shields disposed between the first and second outer side curtain shields and suspended from the frame.

2. The radiation scatter anesthesia protection system of claim 1, wherein the headboard is manufactured from Polyethylene Terephthalate Glycol (PETG).

3. The radiation scatter anesthesia protection system of claim 2, wherein the headboard is formed of a horizontal leg and a vertical leg, and with a longitudinal bend extending along the intersection of the horizontal leg and the vertical leg.

4. The radiation scatter anesthesia protection system of claim 3, wherein the vertical leg is canted inward at an angle x between 5 and 15 degrees, off the perpendicular from the horizontal leg to the vertical leg.

5. The radiation scatter anesthesia protection system of claim 4, wherein the vertical leg is canted inward at an angle of about 10 degrees, off the perpendicular from the horizontal leg to the vertical leg.

6. The radiation scatter anesthesia protection system of claim 2, wherein the plurality of additional sheets of shielding overlap each other and extend across the patient and above the procedure table.

7. The radiation scatter anesthesia protection system of claim 2, wherein the headboard shielding is fastened together, and attached to a plastic sheet.

8. The radiation scatter anesthesia protection system of claim 1, wherein the headboard has a plurality of notches cut into the vertical leg and spaced along a length of the vertical leg and extending from an outer edge of the vertical leg.

9. The radiation scatter anesthesia protection system of claim 8, wherein the horizontal leg of the headboard is inserted under the procedure table mattress, and the vertical leg extends upwardly from the procedure table and is adapted to rest against the patient's head.

10. The radiation scatter anesthesia protection system of claim 8, wherein knobs protrude from the plastic sheet to be temporarily secured within the notches disposed through the headboard, and thereby mount the headboard shielding to the headboard.

11. The radiation scatter anesthesia protection system of claim 10, wherein the sheets of lead-impregnated rubber are covered on a back side and a front side with a sheet of cloth covering that are sewn together around circumference of each of the sheets.

12. The radiation scatter anesthesia protection system of claim 1, wherein the headboard shielding, the first and second outer side curtain shields, and the first and second central curtain shields are constructed of sheets of lead-impregnated rubber.

13. The radiation scatter anesthesia protection system of claim 11, wherein the sheet of cloth covering has a urethane coating on an inside surface against the sheet of lead-impregnated rubber for water proofing.

14. The radiation scatter anesthesia protection system of claim 1, wherein the frame consists of a plurality of interconnected poles to support the first and second outer side curtain shields, and the first and second central curtain shields.

15. A radiation scatter anesthesia protection system designed to attach to a procedure table to limit exposure to radiation for both medical staff and a patient, comprising;
   a headboard of Polyethylene Terephthalate Glycol (PETG) adapted to be disposed adjacent the patient's head,
   headboard shielding including a first sheet of shielding extending downward from the procedure table, a plurality of additional sheets of shielding removably mounted to the headboard, and a molded head shield extending from the headboard;
   a frame disposed adjacent the procedure table;
   first and second outer side curtain shields suspended from the frame;
   the first and second central curtain shields being disposed between the first and second outer side curtain shields and suspended from the frame; and
   the headboard shielding, the first and second outer side curtain shields, and the first and second central curtain shields are constructed of sheets of lead-impregnated rubber.

16. The radiation scatter anesthesia protection system of claim 15, wherein the plurality of additional sheets of shielding overlap each other and extend across the patient and above the procedure table.

17. The radiation scatter anesthesia protection system of claim 16, wherein the headboard shielding is fastened together, and attached to a plastic sheet.

18. The radiation scatter anesthesia protection system of claim 17, wherein knobs protrude from the plastic sheet to be temporarily secured within notches disposed through the headboard, and thereby mount the headboard shielding to the headboard.

19. The radiation scatter anesthesia protection system of claim 18, wherein the sheets of lead-impregnated rubber are covered on a back side and a front side with a sheet of cloth covering that are sewn together around circumference of each of the sheets.

20. The radiation scatter anesthesia protection system of claim 19, wherein the sheet of cloth covering has a urethane coating on an inside surface against the sheet of lead-impregnated rubber for water proofing.

\* \* \* \* \*